United States Patent [19]

Deutsch et al.

[11] Patent Number: 4,606,855
[45] Date of Patent: Aug. 19, 1986

[54] MONOCLONAL ANTIBODY TO DIGOXIN

[75] Inventors: Alice Deutsch, New York; Harvey Brandwein, Port Washington; Herbert Platt, Great Neck; Dianne M. Hunter, New Rochelle; Andrew Dubitsky, Amityville; Susan M. Durham, Westbury, all of N.Y.

[73] Assignee: Mex Research Associates c/o Leon Reimer, White Plains, N.Y.

[21] Appl. No.: 516,483

[22] Filed: Jul. 22, 1983

Related U.S. Application Data

[63] Continuation-in-part of Ser. No. 401,460, Jul. 26, 1982, Pat. No. 4,477,576.

[51] Int. Cl.⁴ .................. G01N 33/53; G01N 33/531; G01N 33/577
[52] U.S. Cl. ...................................... 530/387; 435/68; 435/240; 435/948; 436/548; 935/104; 935/108; 935/110
[58] Field of Search .............................. 436/518–535, 436/500, 510, 808, 810, 815, 807, 817, 548, 823; 435/4–7, 28, 19, 21; 427/68, 240, 61; 935/104, 108, 110

[56] References Cited

U.S. PATENT DOCUMENTS 3,817,837  6/1974  Rubenstein et al. ............... 435/7
4,043,872  8/1977  Blakemore et al. ............... 435/7
4,378,344  3/1983  Zahradnik et al. .

FOREIGN PATENT DOCUMENTS 2500166  8/1982  France ................... 436/536

OTHER PUBLICATIONS

Vos et al, Ann. N.Y. Acad. Sci., vol. 320 (1979), 518–534.
Polin et al, J. Cli. Microbiol., vol. 11(4), 332–336 (1980).
Polin, Monoclonal Antibodies, Ed. Kennett et al, No. 353–359 (1980).
Langone, et al, Ed, Methods in Enzymology, vol. 92 (1983) "Monoclonal Antibodies & General Immunoassay Methods".
McMichael et al, Ed, Monoclonal Antibodies in Clinical Medicine, Academic Press, London (1982).
Engvall et al., J. Immunology, 109(1) 129–135 (1972).
Engvall, Methods in Enzymology, vol. 70, 419–439 (1980).
Voller et al, Immunoenzymatic Assay Techniques, Mal Vano (Ed) ECSC pub. Brussels (1980).

Primary Examiner—Christine M. Nucker
Attorney, Agent, or Firm—Sprung Horn Kramer & Woods

[57] ABSTRACT

A method of determining the concentration of an antigen in a sample solution comprising
(a) coating an antigen-protein conjugate onto a solid matrix,
(b) conjugating an enzyme to an antibody specific for said antigen,
(c) to a known quantity of a solution containing the antibody-enzyme conjugate of (b) adding a specified quantity of a sample containing an unknown amount of the antigen whose content is to be determined,
(d) contacting the coated solid matrix of (a) with the solution (c) and incubate so as to effect binding between the antibody and antigen, some of the antigen being that from the sample and some being that on the solid matrix,
(e) removing the solid matrix from the solution and washing,
(f) immersing the solid matrix in a solution containing a known amount of an enzyme-substrate which is acted upon by the enzyme so as to effect reaction between the enzyme and enzyme-substrate to produce a product, and then separating the solid matrix form the solution of enzyme-substrate, and
(g) then measuring the solid matrix and/or the solution of enzyme-substrate with a pre-established standard to indicate the amount of antigen which was in the sample added in (c).

1 Claim, 4 Drawing Figures

At beginning of step (c) sample containing antigen added to solution containing antibody-enzyme conjugate. Some antibody-enzyme binds to some antigen.

antigen: ▲ antibody-enzyme: ⚹

At end of step (d) antibody-enzyme conjugate binding to antigen in solution and antigen on solid matrix.

antigen-protein conjugate: ◗ antibody-enzyme conjugate: ⚹ antigen: ▲

At step (f) enzyme conjugated to antibody and bound to solid matrix breaks down substrate to produce fluorescent product in solution.

MONOCLONAL ANTIBODY TO DIGOXIN

This is a continuation-in-part of application Ser. No. 401,460 filed on July 26, 1982, now U.S. Pat. No. 4,477,576.

The present invention relates to a novel method of assaying biological materials to ascertain their content of specific substances, as well as to the element for conducting such assays and their preparation.

If one wishes to ascertain the content of a particular drug, e.g. digoxin, in blood or urine, there are various known techniques which may be employed. One can effect complex chemical separations by chromatography and/or chemical reactions to separate the active material and then one can determine the amount by weighing, by radioimmunoassay, or by other techniques.

These procedures give satisfactory results but they are extremely slow and costly. In addition they require a high degree of skill on the part of the operator.

It is accordingly an object of the present invention to provide an assay technique for biological materials, and elements thereof, which can be carried out simply and reliably in a relatively short period of time.

These and other objects and advantages are realized in accordance with the present invention pursuant to which an assay element is produced by (a) conjugating an enzyme to an antibody specific for the antigen to be assayed, (b) attaching or coating an antigen-protein conjugate onto a solid matrix, To conduct the assay, one then proceeds (c) to a known quantity of a solution containing the antibody-enzyme conjugate of (a) adding a specified quantity of a sample containing an unknown amount of the antigen whose content is to be determined, (d) contacting the coated solid matrix of (b) with the solution (c) and incubate so as to effect binding between the unbound antibody and the matrix-bound antigen, (e) removing the solid matrix from the solution and washing, (f) immersing the solid matrix in a solution containing a known amount of an enzyme-substrate which is acted upon by the enzyme so as to effect reaction between the enzyme and enzyme-substrate to produce a detectable product, and then separating the solid matrix from the solution of enzyme-substrate, and (g) then measuring the amount of product formed in (f) and comparing the solid matrix and/or the solution with a pre-established standard to indicate the amount of antigen which was in the sample added in (c).

During step (c) the antigen in the unknown sample binds to some of the antibody-enzyme conjugate. During step (d) some of the remaining antibody-enzyme conjugate not bound to soluble antigen in step (c) now binds to the solid matrix antigen, and an equilibrium is established. In this matter the more antigen in the unknown, the less antibody-enzyme conjugate will be available for binding to the solid-matrix antigen, i.e.—the amount of antigen in the unknown will determine the amount of enzyme on the solid-matrix.

Thus there is produced in step (e) an assay element comprising:

(a) a solid matrix, (b) a multiplicity of protein molecules carried on said matrix, (c) a multiplicity of antigen molecules respectively conjugated to said protein molecules, (d) a plurality of antibody molecules bound to only some of said antigen molecules, and (e) a plurality of enzyme molecules respectively conjugated to said antibody molecules.

This element is then employed to act enzymatically upon the enzyme substrate, the amount of substrate acted upon and resulting product formed being a function of the amount of conjugated enzyme which in turn is a function of the amount of conjugated antibody on the solid matrix which in turn is a function of the amount of antigen in the unknown sample.

Advantageously the enzyme is one which upon an enzyme-substrate will effect a measurable change, e.g. a beta-galactosidase enzyme working on a galactopyranoside residue of a fluorescent material such as umbelliferone. Accordingly, when the beta-galactosidase enzyme is contacted with a known quantity of the umbelliferyl $\beta$-D-galactoside, umbelliferone will be liberated in an amount dependent on the amount of beta-galactosidase enzyme on the solid matrix, i.e. dependent on the amount of antigen which was in the unknown. One then measures the fluorescence of the solution (which is an indication of the amount of umbelliferone formed) and compares it with the fluorescence produced in calibration runs with known amounts of the antigen in step (c); the comparison gives a read-out of the antigen content of the unknown sample.

Alternatively, one could measure the fluorescence on the dipstick, i.e. the solid matrix. Apart from fluorescence, other differences in the wave length of transmitted light could be measured, e.g. optical density, color, light transmission, etc., using appropriate substrates, enzymes, etc.

These steps will now be further described in detail in combination with the accompanying drawings wherein.

The antigen which is to be assayed can be a drug such as digoxin, theophylline, or phenytoin, or other biologically active substance such as a hormone or a molecule present on a cell, a parasite, virus, or other organism. This is conjugated with any substance which, in turn, can be joined to a solid matrix in step (b). A suitable inexpensive solid matrix is a simple plastic dipstick, e.g. polystyrene, to which proteins adhere without special treatment. Alternatively, chemical treatment may be used to enhance antigen-protein binding. Other substances such as paper, cellulose acetate, plastics, etc., can be employed instead.

The substance which will serve to "anchor" the antigen to the solid matrix will of course depend upon the particular antigen and solid matrix but proteins have proven especially useful both because of performance, cost and availability. Albumin and especially bovine serum albumin (BSA) is quite suitable, adhering readily to polystyrene.

Conjugation of the antibody to the enzyme in (a) can be effected in a conventional manner using linking agents such as glutaraldehyde and other bi- and polyfunctional compounds which produce a chemical bond while leaving intact both the antibody and enzyme activity.

The antibody employed in step (c) is of course dependent upon the antigen employed in (b), i.e. the antigen to be assayed, since it must bind therewith. For best results it is desirable that the antibody be a monoclonal antibody produced in known manner from mouse spleen cells fused with myeloma cells, as described more fully hereinbelow. The use of monoclonal antibodies gives the most reproducible results.

Figure 1:
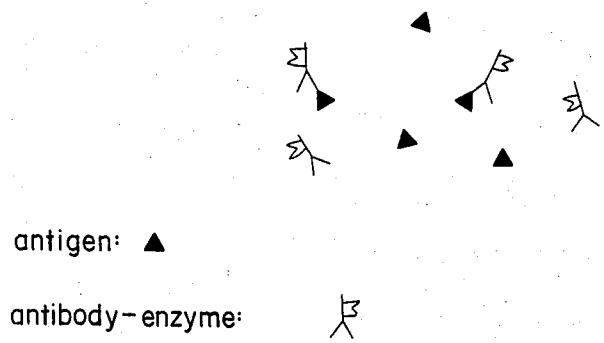
FIG. 1 is a schematic illustration of the system at the beginning of step (c)
Figure 2:
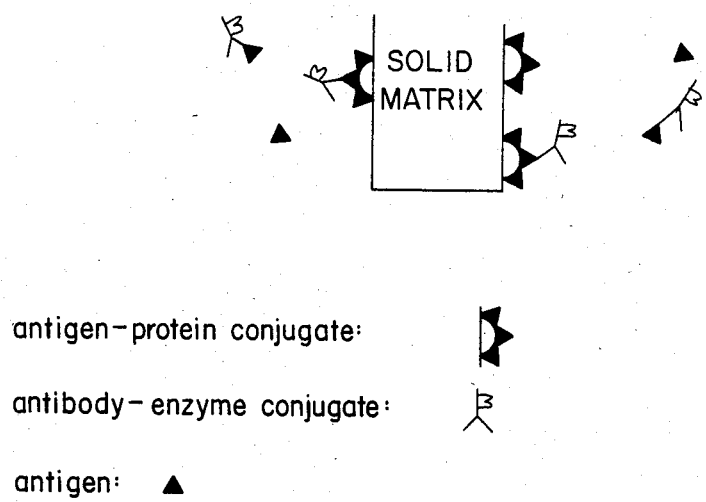
FIG. 2 is a schematic illustration of the system at the end of step (d)

Desirably the binding in step (d) is completed in a few minutes at room or slightly elevated temperature, e.g. about 10 minutes at 37° C. FIG. 1 shows the interaction between the antigen from the unknown and the antibody-enzyme conjugate. In FIG. 2 some of the antibody-enzyme conjugate which did not bind in step (c) has bound with solid matrix antigen, reaching an equilibrium between the two antigen sources.

Figure 3:
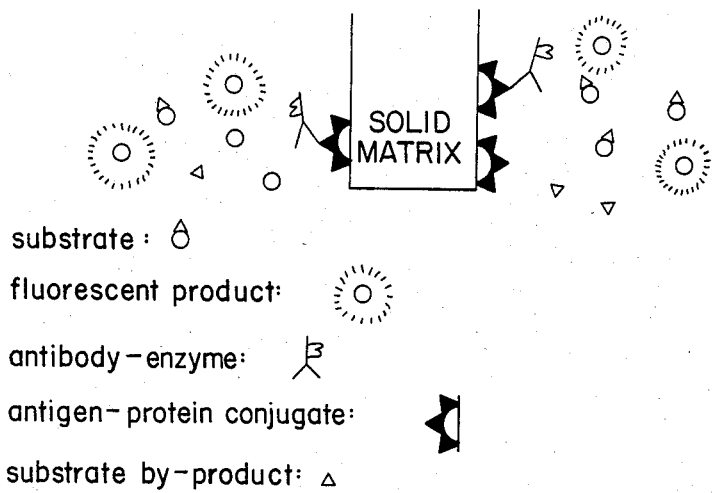
FIG. 3 is a schematic illustration of step (f)

The identity of the enzyme-substrate in (f) of course depends upon the enzyme in (a). The enzyme must be one capable of conjugating to the antibody and must also be capable of producing a quick, easily metered change in the enzyme substrate. Alkaline phosphatases, $\beta$-galactosidases, peroxidases and esterases have proven quite satisfactory. For example, with a $\beta$-galactosidase one can employ an enzyme-substrate which has a galactopyranoside residue of a fluorescent compound such as umbelliferone. Accordingly incubation of the enzyme-substrate releases umbelliferone ("Product" in FIG. 3) into the solution which in turn causes the solution to fluoresce. This fluorescense can be measured with a fluorimeter and, by prior calibration with samples containing known quantities of the antigen (FIG. 4), can directly indicate the amount of antigen in the unknown.

Figure 4:
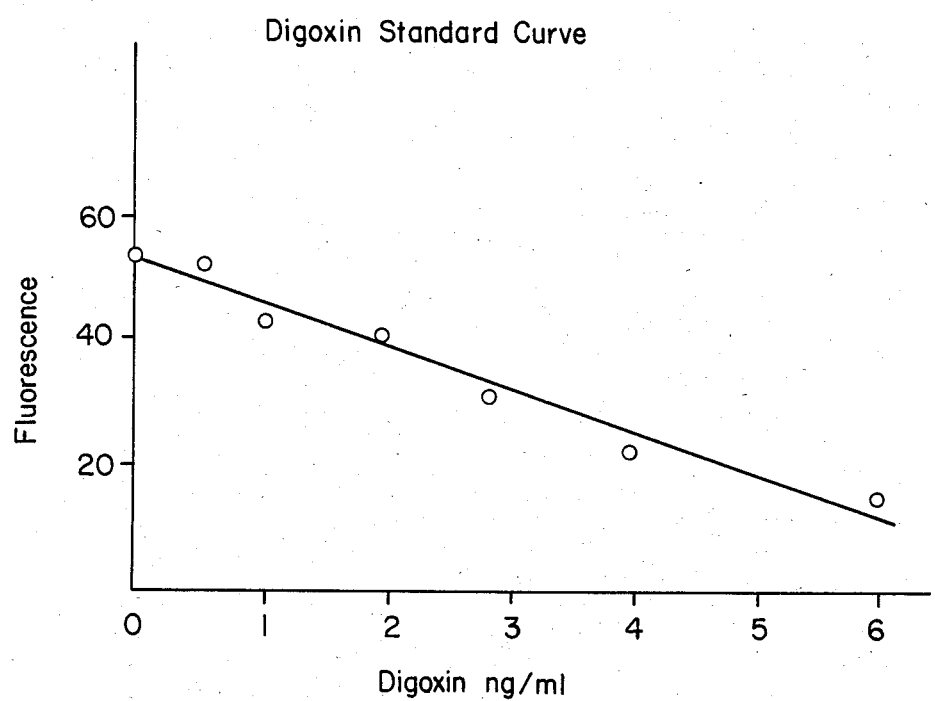
FIG. 4 is a curve used in carrying out step (g).

It is an advantage of the present invention that the curve in FIG. 4 is relatively straight which means greater reliability in reading at all concentrations of unknown.

The procedure lends itself to ready adoption by providing a kit comprising (i) a dipstick already carrying the antigen, (ii) a solution of antibody conjugated to enzyme, (iii) a series of test tubes containing wash solutions in which to dip the dipstick after step (d), and a test tube containing a predetermined amount of enzyme-substrate.

For calibration purposes one can also supply a series of "knowns" containing specific amounts of the antigen, permitting a fluorescence curve to be drawn for the particular fluorimeter being used.

The invention will now be described in greater detail in the following illustrative example:

EXAMPLE

(a) Immunization

Each Balb/c mouse was immunized with 10 $\mu$g of digoxin-bovine serum albumin (BSA) conjugate (obtained from Immunotech) in 50 mM tris-HCl buffer pH 7.6 in Freund's complete adjuvant. A month later each mouse was injected with 10 $\mu$g of digoxin-BSA in phosphate-buffered saline. Four days later the spleens were removed for fusing.

(b) Cell Fusion and Hybridoma Production

The techniques of Kohler and Milstein (1975) were used to obtain monoclonal antibodies. Spleen cells were fused with $1.5 \times 10^7$ myeloma cells as described by Kennet (1980) using 37% polyethylene glycol (molecular weight=1000). After the fusion the washed cells were suspended in complete medium containing hypoxathine, aminopterin, and thymidine (Littlefield 1964) and distributed into all the wells of ten 96-well plates. Wells with hybridoma cells were screened for production of antibody specific for digoxin. Positive wells were then cloned in 0.5% agarose with complete medium. After 10 days clones were isolated and transferred to liquid medium for further growth in microwells. The resultant monoclonal populations were injected into mice primed with 0.5 ml pristane two weeks prior to intraperitoneal injection of $5 \times 10^6$ hydridoma cells.

The monoclonal antibody has been deposited with the American Type Culture Collection, identified as HB 8319, date of deposit July 15, 1983.

(c) Indirect Binding Assay

Supernatants from wells with growing cells were screened for the presence of antibody binding to digoxin and, as a control, BSA. 500 ng of digoxin-BSA in 50 mM bicarbonate buffer pH 9.6 were added to each well of an Immulon 2 plate (purchased from Dynatech). Buffer alone was added to control wells. After overnight incubation at 4° C., the plate was washed with 0.05% BSA/PBS and then incubated with 1% BSA/PBS 30 minutes at room temperature. The plates were washed, 50 microliters of supernatant was added to each well, and the plate was incubated for 1 hour at 37° C. After washing, 60 microliters of 1:100 dilution of goat anti-rabbit peroxidase conjugate (purchased from Microbiological Associates) was added to each well and the plate was incubated for 1 hour at room temperature. After washing, 100 microliters of substrate, containing 2,2'-azino-di-(3-ethylbenzthiazoline sulphonic acid) and 0.03% $H_2O_2$ in 0.1M citrate buffer pH 4.2, was added to each well. The contents of each well were measured spectrophotometrically at 420 nm.

(d) Antibody-Enzyme Conjugation

The ascites fluid containing antibody was purified by diluting an 0.14M potassium phosphate buffer pH 8.1 and running over a protein A-Sepharose 4B (Pharmacia) column, washing in the same buffer, and eluting with 0.1M citrate buffer pH 3.2. The antibody was dialyzed against PBS. The method of Carlsson et al. (1978) was used to conjugate the antibody to the enzyme $\beta$-galactosidase (purchased from Boehringer-Mannheim). A solution containing 2 mg purified antibody in 1500 microliters PBS was mixed with 16 microliters of 4 mM N-succinimidyl 3-(2-pyridyldithio) propionate (SPDP) in ethanol for 30 minutes at room temperature. This solution was immediately run over a desalting column. The modified antibody was mixed with 5 mg $\beta$-galatosidase overnight at room temperature.

(e)

The mixture was then dialyzed against phosphate-buffered saline solution to remove free pyridine-2-thione from the remaining solution of antibody-enzyme conjugate. To the solution there were added bovine serum albumin as additional protein carrier, magnesium chloride as a source of divalent cation and sodium azide as a preservative, bringing the solution to a final weight-/volume concentration of 5% bovine serum albumin and 0.01% sodium azide and 1 millimolar $MgCl_2$.

(f)

A polystyrene dipstick was immersed in a solution containing 10 $\mu$g/ml of digoxin conjugated to bovine serum albumin (conjugate purchased from Immunotech) in 50 mM of sodium bicarbonate pH 9.8. The stick and solution were incubated for 16 hours at 4° C. and then the stick was placed and held for 15 minutes in a blocking phosphate-buffered saline solution containing 1% of bovine serum albumin.

(g)

100 microliters of a solution containing 1 nanogram/ml of digoxin in phosphate buffered saline solution were added to 500 microliters of the solution obtained in (d) and incubated at 37° C. The dipstick was then removed from the solution in (f) and washed by being dipped successively into four saline solutions each containing 1% bovine serum albumin and 0.01% sodium azide, buffered with phosphate.

(h)

The dipstick was then dipped into 1 ml of a solution of 100 micromolar methyl umbelliferyl-$\beta$-D-galactoside, 1% bovine serum albumin buffered with phosphate and 1 millimolar magnesium chloride. The solution and dipstick were incubated at 37° C. for 5 minutes, the dipstick was removed and discarded, and the remaining solution in a cuvette was placed in a Perkin-Elmer Fluorimeter Model No. 650-10S, giving a reading of 48.

(i)

The procedures of (g) and (h) were repeated with the sole difference that the digoxin solution in successive runs was 2 nanograms/ml, 3 nanograms/ml, etc., up to 10 nanograms/ml and the fluorimeter readings were plotted against the antigen concentration as shown in FIG. 4.

(j)

The procedures of (g) and (h) were then repeated using 100 microliters of a serum specimen containing an unknown quantity of digoxin. This sample eventually gave a fluorimeter reading of 40, indicating a digoxin content of 2 nanograms/ml. This agrees closely with analysis of the same sample by radioimmunoassay.

By substantially the same procedure using appropriately specific antibodies the following antigens were assayed and the results obtained agreed with radioimmunoassay:
progesterone
estrogens (estriol, $\beta$-estradiol and estrone)
thyroxine
dilantin(phenytoin)
theophylline
digitoxin
Others which can be similarly assayed include:
T-3 (triiodothyronine)
canine heartworm
canine heartworm antibodies
vira
herpes simplex virus
peptides and polypeptides
sugar residues (saccharides)
glycoproteins
proteins
steroids
nucleic acids such as RNA and DNA
modified aminoacids
glycolipids The necessary materials for carrying out the analysis can be combined into a kit so the operator need not mix any chemicals. For example, the kit can consist of six sealed plastic cuvettes or test tubes and one dipstick soaking in wash solution (Example g) and sealed in plastic. The dipstick already carries the protein and antigen as in Example b.

Cuvette 1 contains 500 microliters of antibody-enzyme conjugate as in Example a, while Cuvettes 2, 3, 4 and 5 each contain 1 ml of the wash solution. Cuvette 6 contains 1 ml of the umbelliferyl-$\beta$-D galactoside substrate solution.

The operator adds 100 microliters of the unknown sample to Cuvette 1, incubates for 10 minutes at 37° C., adds the dipstick to Cuvette 1 and incubates the cuvette at 37° C. for an additional 5 minutes. The dipstick is removed, successively immersed in Cuvettes 2, 3, 4, 5 and 6 and Cuvette 6 with dipstick is incubated for 5 minutes at 37° C. The dipstick is discarded and Cuvette 6 is placed in the fluorimeter and read. It is possible to calibrate the fluorimeter so it directly indicates the digoxin (or other antigen) concentration in the unknown.

It is even possible to prepare the fluorimeter to hold all six cuvettes side-by-side as a single module.

It will be understood that the specification and example are illustrative but not limitative of the present invention and that other embodiments within the spirit and scope of the invention will suggest themselves to those skilled in the art.

What is claimed is:

1. The digoxin monoclonal antibody produced by cell line HB 8319.

* * * * *